United States Patent
Brewster et al.

(10) Patent No.: US 11,197,879 B2
(45) Date of Patent: *Dec. 14, 2021

(54) FLAVONOID COMPOSITIONS AND USES THEREOF

(71) Applicants: INGREDIENTS BY NATURE, Montclair, CA (US); U.S. DEPARTMENT OF AGRICULTURE, Beltsville, MD (US)

(72) Inventors: Robert M. Brewster, Montclair, CA (US); John A. Manthey, Fort Pierce, FL (US)

(73) Assignees: INGREDIENTS BY NATURE, Montclair, CA (US); THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 20 days.

This patent is subject to a terminal disclaimer.

(21) Appl. No.: 16/784,010

(22) Filed: Feb. 6, 2020

(65) Prior Publication Data

US 2020/0246367 A1    Aug. 6, 2020

Related U.S. Application Data

(62) Division of application No. 15/300,866, filed as application No. PCT/US2015/023650 on Mar. 31, 2015.

(60) Provisional application No. 61/972,934, filed on Mar. 31, 2014.

(51) Int. Cl.
  *A61K 31/7048* (2006.01)
  *A61P 3/10* (2006.01)
  *A61K 31/353* (2006.01)
  *C07D 311/32* (2006.01)

(52) U.S. Cl.
  CPC ........ *A61K 31/7048* (2013.01); *A61K 31/353* (2013.01); *A61P 3/10* (2018.01); *C07D 311/32* (2013.01)

(58) Field of Classification Search
  CPC ...... A61K 31/7048; C07D 311/32; A61P 3/10
  See application file for complete search history.

(56) References Cited

U.S. PATENT DOCUMENTS

2007/0244189 A1   10/2007   Fukumoto et al.
2011/0159151 A1   6/2011    Koike et al.

FOREIGN PATENT DOCUMENTS

JP    2005-198642        7/2005
WO    2012/016148 A1    2/2012
WO    2013086323 A2     6/2013

OTHER PUBLICATIONS

Hiramitsu, M. et al., Scientific Reports, "Eriocitrin ameliorates diet-induced hepatic steatosis with activation of mitochondrial biogenesis", 2014, vol. 4, 11 pages (Year: 2014).*
Miyake, Y. et al., Lipids, "Protective Effects of Lemon Flavonoids on Oxidative Stress in Diabetic Rats", 1998, vol. 33, No. 7, pp. 689-698 (Year: 1998).*
Shams-Rad, S., et al., "Hesperidin Supplementation Has No Effect on Blood Glucose Control: A Systematic Review and Meta-Analysis of Randomized Controlled Clinical Trials," Br J Clin Pharmacol (Sep. 6, 2019).
Hamdan, D., et al., "Effect of Hesperidin and Neohesperidin from Bittersweet Orange (*Citrus Aurantium* var. *bigaradia*) Peel on Indomethacin-Induced Peptic Ulcers in Rats," Environmental Toxicology and Pharmacology, vol. 37, pp. 907-915 (2014).
Ogden, C., et al., "Mean Body Weight, Height, and Body Mass Index, United States 1960-2002," Advance Data from Vital and Health Statistics, No. 347, pp. 1-18 (Oct. 27, 2004).
Mahmoud, A., "Hesperidin and Naroiingin Attenuate Hyperglycemia-Mediated Oxidative Stress and Proinflammatory Cytokine Production in High Fat Fed/Streptozotocin-Induced Type 2 Diabetic Rats," Journal of Diabetes and Its Complications, vol. 26, pp. 483-490 (2012).
Second Declaration of Thais Cesar, Ph.D., dated Dec. 15, 2019.

\* cited by examiner

*Primary Examiner* — Bahar Craigo
(74) *Attorney, Agent, or Firm* — Polsinelli PC; Ron Galant (57) ABSTRACT

This invention relates to a flavonoid composition that includes eriocitrin. The flavonoid may be included in a complex with other bioflavonoids. The composition may also include neoeriocitrin. This invention also relates to methods of using the composition, including for reducing IL-6 or MCP-1 treating inflammation, and treating symptoms of metabolic syndrome.

16 Claims, 4 Drawing Sheets

FLAVONOID COMPOSITIONS AND USES THEREOF

FIELD OF THE INVENTION

The present invention relates to compositions comprising eriocitrin, and their use for reducing IL-6 or MCP-1 levels, and as anti-oxidants and anti-inflammatory agents.

BACKGROUND OF THE INVENTION

Inflammation is associated with a number of diseases and conditions, including cardiovascular disease, pain, rheumatoid arthritis, contusion injuries, ulcerative colitis, Crohn's disease, diabetes, and cancer. Tumor necrosis factor alpha (TNFα) is a major proinflammatory cytokine that is involved in the pathogenesis of chronic inflammatory disease. It is modulated by oxidative stress. TNFα expression is regulated through a signaling cascade that is triggered by the inducible transcription factor NF-kB. Given the prominence of inflammation in a number of diseases, inhibiting inflammation, such as by inhibiting NF-kB, provides a promising route to alleviating pain and suffering associated with inflammation.

Additionally, elevated IL-6 levels are associated with a number of diseases and conditions, including autoimmune diseases, chronic inflammatory diseases, obesity, cardiovascular diseases, and cancer. Similarly, MCP-1 levels are elevated in diseases and conditions including metabolic disorders like obesity and diabetes, cardiovascular diseases, and cancer. Reducing elevated levels of either IL-6 or MCP-1 could be used to treat these various diseases and conditions.

Flavonoids are structurally heterogeneous, polyphenolic compounds that are present at high concentrations in fruits, vegetables, and other plant derived foods. These compounds have anti-inflammatory and anti-oxidant properties, and their consumption is associated with health benefits. Flavonoids have been shown to be capable of regulating cell signaling pathways, including TNFα through NF-kB inhibition. Certain inflammatory cytokines are elevated in various diseases and conditions. Accordingly, there is a need in the art for flavonoid compositions for use in reducing IL-6 or MCP-1 levels, inhibiting inflammation, and treating symptoms of metabolic syndrome, and as anti-oxidants.

SUMMARY OF THE INVENTION

Provided herein is a composition comprising at least 10% wt/wt eriocitrin, which may comprise 50% wt/wt eriocitrin. The composition may also comprise at least 0.1% wt/wt of a second flavonoid, which may be neoeriocitrin, eriodictyol, hesperidin, or eriodictyol glucoside. The second flavonoid may be neoeriocitrin, which may be present in amount of at least 0.2% wt/wt neoeriocitrin. The composition comprising eriocitrin and neoeriocitrin may further comprise eriodictyol and/or hesperidin, and/or may further comprise a polymethoxylated flavone, naringen, naringenin, an omega-3 fatty acid, coenzyme Q10, or a green tea extract.

Further provided herein is a method for treating inflammation, comprising the composition to a subject in need thereof. Also provided herein is a method for treating a disease or condition associated with elevated IL-6 levels, comprising administering the composition to a subject in need thereof, wherein the IL-6 levels in the subject are elevated relative to healthy subject. The disease or condition may be an autoimmune disease, a chronic inflammatory disease, a cancer, obesity, type II diabetes, neuromyelitis optica, chronic liver disease, chronic kidney disease, cardiovascular disease, non-ST elevation myocardial infarction, or coronary artery disease.

Also provided herein is a method for treating a disease or condition associated with elevated MCP-1 levels, comprising administering the composition to a subject in need thereof, wherein the MCP-1 levels in the subject are elevated relative to a healthy subject. The disease or condition may be macular degeneration, cardiovascular disease, atherosclerosis or restenosis after angioplasty, a cancer, prostate cancer, inflammation, pancreatitis, a metabolic disorder, inflammation, or pain associated with inflammation. Further provided herein is a method for reducing glucose, insulin, LDL, or hs-CRP levels, comprising administering the composition to a subject in need thereof.

DETAILED DESCRIPTION

The inventors have made the surprising discovery that the eriocitrin compositions described herein (1) strongly reduce levels of IL-6 and MCP-1 (Chemokine (C-C motif) ligand 2 (CCL2)); (2) are potent inhibitors of NF-kB; and, (3) have strong anti-oxidant properties. Accordingly, the composition can be used to treat diseases and conditions associated with elevated IL-6 or MCP-1 levels, and to treat inflammation as an anti-oxidant. The compositions can also be used treat symptoms of metabolic syndrome, such as by reducing glucose, insulin, or C-reactive protein levels, or by improving lipid levels, such as reducing total cholesterol, low-density lipoprotein, or triglyceride levels, or increasing high-density lipoprotein levels. The composition may have particular use in nutritional supplements or as a food additive.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6,9, and 7.0 are explicitly contemplated.

"About" may mean ±50% of a recited amount. About may also mean ±10% of a recited amount.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

2. Flavonoid Composition

Provided herein is a composition comprising a flavonoid, which may be eriodictyol, eriocitrin, neoeriocitrin, hesperidin, diosmin, hesperetin, naringin, naringenin, narirutin, or didymin, or a combination thereof. In particular, the composition may comprise eriocitrin and neoeriocitrin. The flavonoid may be derived, purified, or isolated from a fruit, plant, herb, or other food source. The fruit may be a citrus, such as a lemon. The eriocitrin may have the structure eriodictyol 7-O-B-rutinoside. The neoeriocitrin may have the structure eriodictyol-7-O-neohesperidoside. The composition may be ERIO™ or ERIOMIN™.

a. Eriodictyol

The composition may comprise eriodictyol. The eriodictyol may be 3',4',5,7-tetrahydroxyflavanone, and may have the following structure.

The eriodictyol may be the parent aglycone of eriocitrin. The composition may comprise at least 80, 85, 90, 91, 92, 93, 94, 95, 96, 97, 98, or 99% wt/wt eriodictyol. The eriodictyol may be derived from eriocitrin through a conversion process.

The eriodictyol may be a complex. The complex may comprise other flavonoids, which may include eriocitrin, hesperidin, diosmin, hesperetin, and/or naringenin. The other flavonoids may be present in the composition in an amount of at least about 0.05, 0.1, 0.2, 0.3, 0.4, 0.5, 0.6, 0.7, 0.8, 0.9, 1, 2, 3, 4, 5, 6, 7, 8, 9, or 10% wt/wt. The complex may comprise about 91% wt/wt eriodictyol, 0.4% wt/wt eriocitrin, 1% wt/wt hesperidin, 0.3% wt/wt diosmin, 3% wt/wt hesperetin, and 2% wt/wt naringenin.

b. Eriocitrin

The composition may comprise eriocitrin, which may be a complex. The composition may comprise at least about 10, 20, 30, 40, 50, 60, 65, 70, 75, 80, 85, 90, 95, 96, 97, 98, or 99% wt/wt eriocitrin. The composition may also include eriocitrin as the only flavonoid, so that the flavonoid in the composition is pure or substantially pure eriocitrin. Substantially pure in this context may mean that the flavonoids in the composition are at least about 50, 55, 60, 65, 70, 75, 80, 85, 90, 95, 99.0, 99.1, 99.2, 99.3, 99.4, 99.5, 99.6, 99.7, 99.8, or 99.9% wt/wt eriocitrin. The complex may comprise other flavonoids, which may include narirutin, hesperidin, didymin, naringenin, and/or hesperetin. The other flavonoids may be present in the composition in an amount of at least about 0.1, 0.2, 0.3, 0.4, 0.5, 0.6, 0.7, 0.8, 0.9, 1, 2, 3, 4, 5, 6, 7, 8, 9, or 10% wt/wt.

c. Neoeriocitrin

The composition may comprise neoeriocitrin, and may comprise at least about 0.1, 0.2, 0.3, 0.4, 0.5, 1, 2, 3, 4, 5, 6, 7, 8, 9, 10, 11, 12, 13, 14, 15, 16, 17, 18, 19, or 20% wt/wt neoerioctrin.

d. Eriodictyol Glucoside

The composition may comprise eriodictyol glucoside, and may comprise at least about 0.1, 0.2, 0.3, 0.4, 0.5, 1, 2, 3, 4, 5, 6, 7, 8, 9, 10, 11, 12, 13, 14, 15, 16, 17, 18, 19, or 20% wt/wt eriodictyol glucoside.

e. ERIOMIN™

The ERIOMIN™ composition may comprise a plant flavonoid as described herein. The ERIOMIN™ may comprise about 10-70% eriocitrin as the only plant flavonoid in the composition. The ERIOMIN™ may comprise about 10-70% wt/wt eriocitrin and 0.2-20% wt/wt neoeriocitrin, and may further comprise hesperidin. The ERIOMIN™ composition may comprise about 5-30% wt/wt eriocitrin, 0.05-5% wt/wt neoerioctrin, and 20-60% hesperidin. The ERIOMIN™ composition may also comprise about 10-25% wt/wt eriocitrin, 0.5-2.5% wt/wt neoeriocitrin, and 25-50% wt/wt hesperidin. The ERIOMIN™ composition may comprise about 15% wt/wt eriocitrin, 1.5% wt/wt neoeriocitrin, and 33.5% wt/wt hesperidin. The ERIOMIN™ composition may also comprise about 25% wt/wt eriocitrin, 1.5% wt/wt neoeriocitrin, and 33.5% wt/wt hesperidin.

f. Additional Agents

The composition may also comprise an additional agent, which may be an omega-3 fatty acid, a plant extract, a coenzyme, a flavonoid, a polymethoxylated flavone (PMF), a limonoid, or a green tea extract. The omega-3 fatty acid may be in an ethyl ester or triglyceride form. The plant extract may be of *Eurycoma longifolia* or Tongat Ali. The coenzyme may be Coenzyme Q10 (CoQ10). The flavonoid may be quercetin dihydrate. The PMF may comprise a hydroxylated polymethoxylated flavone (HO-PMF). The limonoid may be citrus-derived.

The agent may also be a compound or protein capable of reducing IL-6 levels. The IL-6 level reducer may be an anti-IL-6 antibody, an anti-IL-6-receptor (IL-6-R) antibody, or an IL-6-R ligand. The anti-IL-6 antibody may be siltuximab, sirukumab, sarilumab, ALD518/BMS-945429, CPSI-2364, VX30, ARGX-109, FE301, FM101, or B-E8/mAb 133. The anti-IL-6-R antibody may be tocilizumab or REGN-88.

The agent may also be a compound or protein capable of reducing MCP-1 levels. The MCP-1 level reducer may be an anti-MCP-1 antibody, a methanolic extract from unripe kiwi fruit, an ethanolic extract from bamboo leaves, mulberry, dehydroabetic acid, capsaicin, curcumin, diallyl disulfide, allyl isothiocyanate, piperine, zingerone, a procyanidin, berberine, resveratrol, acarbose, propagermanium, chromium niacinate, L-cysteine, troglitazone, rosiglitazone, atorvastatin, simvastatin, pravastatin, cerivastatin, dilazep, fenofibric acid, HE3286, TEI-K03134, ARB L158809, aspirin, clofibrate, gliclazide, irbesartan, olmesartan medoxomil, valsartan, telmisartan, PD123319, pyrrolidine dithiocarbamate, doxazosin, D-psicose, a plant extract from *Erigeron multiradiatus* (Lindl.) Benth, an aqueous extract of *Buddleja officinalis*, enalapril, mycophenolate mofetil, lisinopril, spironolactone, mizoribine, LY333531, cilostazol, colestimide, insulin, triptolide, lithospermic acid B, breviscapine, azuki bean seed coats, retinoic acid, vitamin E, astaxanthin, eicosapentaenoic acid, canola oil, kremezin/AST-120, or low-dose radiation.

The composition may comprise the ERIOMIN™ and one or more of diosmin, diosmetin, naringin, naringenin, a PMF, a HO-PMF, a limonoid, curcumin, a green tea extract, a grapeseed extract, an omega-3 fatty acid, a CoQ10, resveratrol, vitamin D, vitamin C, quercetin, and rutin. The composition may comprise the ERIOMIN™ and vitamin C. The composition may also comprise the ERIOMIN™ and resveratrol, or the ERIOMIN™ and the green tea extract.

g. Dose

The composition may comprise a dose of the plant flavonoid and/or additional agent of about 15-2000 mg. For example, composition may comprise about 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, or 2000 mg of the plant flavonoid and/or additional agent.

For example the composition may comprise eriocitrin at a dose of 15-2000 mg. The composition may comprise about 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, or 2000 mg eriocitrin.

The composition may comprise 50-500 mg plant flavonoids comprising eriocitrin, which may be the ERIOMIN™ composition, and may comprise about 250 or 500 mg of the plant flavonoids. The composition may also comprise 50-500 mg of the additional agent, which may be a green tea extract, resveratrol, a PMF, a HO-PMF, a limonoid, curcumin, a grapeseed extract, an omega-3 fatty acid, a CoQ10, vitamin D, vitamin C, quercetin, or rutin. The composition may comprise 50, 100, 150, 200, 250, or 500 mg of the additional agent. In particular, the composition may comprise about 250 or 500 mg of the plant flavonoids and about 50, 100, 200, 250, or 500 mg of the green tea extract or resveratrol.

h. Formulation

The composition may be included in a formulation such as an oral formulation. The formulation may be a self-assembling colloidal delivery system such as the VESISORB® system (Vesifact AG, Zurich, Switzerland), which may be as described in U.S. Patent Publication No. 20060292191, 20050191330, 20040152612, 20030190347, or 20020106390, or U.S. patent application Ser. No. 10/110,212, the contents of which are incorporated herein by reference.

The composition may be in the form of tablets or lozenges formulated in a conventional manner. For example, tablets and capsules for oral administration may contain conventional excipients including a binding agent, filler, lubricant, disintegrant or wetting agent. The binding agent may be syrup, accacia, gelatin, sorbitol, tragacanth, mucilage of starch or polyvinylpyrrolidone. The filler may be lactose, sugar, microcrystalline cellulose, maize starch, calcium phosphate, or sorbitol. The lubricant may be magnesium stearate, stearic acid, talc, polyethylene glycol, or silica. The disintegrant may be potato starch or sodium starch glycollate. The wetting agent may be sodium lauryl sulfate. Tablets may be coated according to methods well known in the art. The composition may be formulated as a soft gelatin formulation. The soft gelatin may comprise one or more of gelatin, purified water, glycerin, soy lecithin, beeswax, annatto, silicon dioxide, and titanium dioxide.

The composition may also be a liquid formulation such as an aqueous or oily suspension, solution, emulsion, syrup, or elixir. The composition may also be formulated as a dry product for constitution with water or other suitable vehicle before use. Such liquid preparations may contain an additive such as a suspending agent, emulsifying agent, nonaqueous vehicle or preservative. The suspending agent may be sorbitol syrup, methyl cellulose, glucose/sugar syrup, gelatin, hydroxyethylcellulose, carboxymethyl cellulose, aluminum stearate gel, or hydrogenated edible fat. The emulsifying agent may be lecithin, sorbitan monooleate, or acacia. The nonaqueous vehicle may be an edible oil, almond oil, fractionated coconut oil, oily ester, propylene glycol, or ethyl alcohol. The preservative may be methyl or propyl p-hydroxybenzoate or sorbic acid.

The composition may also be formulated as a suppository, which may contain a suppository base such as cocoa butter or glycerides. The composition may also be formulated for inhalation, which may be in a form such as a solution, suspension, or emulsion that may be administered as a dry powder or in the form of an aerosol using a propellant, such as dichlorodifluoromethane or trichlorofluoromethane. The composition may also be formulated in a transdermal formulation comprising an aqueous or nonaqueous vehicle such as a cream, ointment, lotion, paste, medicated plaster, patch, or membrane.

The composition may also be formulated for parenteral administration such as by injection, which may be intraperitoneal, or continuous infusion. Formulations for injection may be in the form of suspensions, solutions, or emulsions in oily or aqueous vehicles, and may contain a formulation agent such as a suspending, stabilizing, or dispersing agent. The composition may also be provided in a powder form for reconstitution with a suitable vehicle including sterile, pyrogen-free water.

The composition may also be formulated as a depot preparation, which may be administered by implantation or by intramuscular injection. The composition may be formulated with suitable polymeric or hydrophobic materials (as an emulsion in an acceptable oil, for example), ion exchange resins, or as sparingly soluble derivatives (as a sparingly soluble salt, for example).

The composition may also be formulated as a liposome preparation. The liposome preparation may comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used. The composition may be intended to target skin conditions. The composition may comprise niosomes. Niosomes are lipid vesicles similar to liposomes, with membranes consisting largely of non-ionic lipids, some forms of which are effective for transporting compounds across the stratum corneum.

i. Nutritional Supplement and Food Additive

The composition may also be used as a food additive, such as in the manufacture of a functional food or beverage. The composition may also be used in a nutritional supplement.

3. Methods of Use

The composition may be used in a method for treating a disease or condition, which may comprise administering the composition to a subject in need thereof. The subject may be an animal, which may be a mammal such as a human.

a. Reducing IL-6 Levels

The disease or condition may be associated with elevated IL-6 levels, which may be elevated in comparison to a healthy animal. The disease or condition may be an autoimmune disease, a chronic inflammatory disease, or a cancer. The autoimmune or chronic inflammatory disease may be rheumatoid arthritis, systemic juvenile idiopathic arthritis, Castleman's disease, systemic lupus erythematosus, systemic sclerosis, polymyositis, vasculitis syndrome, giant cell arteritis, Takayasu arteritis, cryoglobulinemia, myeloperoxidase-antineutrophil cytoplasmic antibody-associated crescentic glomerulonephritis, rheumatoid vasculitis, Crohn's disease, relapsing polychondritis, acquired hemophilia A, Grave's ophthalmopathy, or autoimmune hemolytic anemia. The chronic inflammatory disease may be adult-onset Still's disease, amyloid A amyloidosis, polymyalgia rheumatica, remitting seronegative symmetrical synovitis with pitting edema, Behcet's disease, uveitis, graft-versus-host disease, tumor necrosis factor receptor-associated periodic syndrome, spondyloarthritis, pulmonary arterial hypertension, atopic dermatitis, Ankylosing spondylitis, Alzheimer's disease, a brain disorder, which may not be psychiatric, or sciatica.

The cancer may be colorectal, ovarian, a hematological malignancy, lymphoma, Hodkin's disease, Non-Hodgkin's lymphoma, a B-cell malignancy, a B-cell leukemia, multiple myeloma, pleural effusion lymphoma, leukemia, or hepatocellular carcinoma. The multiple myeloma may be relapsed or refractory. The disease or condition may be obesity, type II diabetes, neuromyelitis optica, chronic liver disease, or chronic kidney disease. The disease or condition may also be cardiovascular disease, non-ST elevation myocardial infarction, or coronary artery disease.

b. Reducing MCP-1 Levels

The disease or condition may be associated with elevated MCP-1 levels, which may be elevated in comparison to a healthy animal. The disease or condition may be macular degeneration, cardiovascular disease, atherosclerosis or restenosis after angioplasty, a cancer, prostate cancer, inflammation, pancreatitis, or a metabolic disorder. The metabolic disorder may be obesity, diabetes, diabetic neuropathy, or renal injury.

c. Anti-Inflammatory

The disease or condition may be inflammation. The inflammation may be the result of an activity that increases the inflammatory response as a consequence of repetitive muscle contraction or high rates or volumes of oxygen uptake. The inflammation may also result from a muscle or contusion injury. The inflammation may also be inflammatory disease or condition such as chronic or silent inflammation, arthritis, rheumatoid arthritis, Alzheimer's disease, sepsis, atherosclerosis, cardiovascular disease, ischemia, stroke, coronary artery disease, peripheral vascular disease, heart attack, asthma, chronic obstructive pulmonary disease, an autoimmune disorder, Crohn's disease, tendinitis, bursitis, gouty arthritis, polymyalgia rheumatica, and ulcerative colitis. The disease or condition may also be pain associated with inflammation.

d. Antioxidant

The composition may be used as an antioxidant, and the disease or condition may be cancer, cardiovascular disease, Alzheimer's disease, Parkinson's disease, diabetes, rheumatoid arthritis, or neurodegeneration.

e. Inhibiting NF-kB

The composition may inhibit NF-kB, which may be performed by contacting a cell with the composition. Inhibition of NF-kB may also be inhibited by administering the composition to a mammal in need thereof.

f. Metabolic Syndrome

The disease or condition may be a symptom associated with a metabolic syndrome. The composition may reduce blood glucose levels, which may be fasting blood glucose. The composition may reduce fasting insulin levels, which may be fasting insulin levels. The composition may improve lipid levels, which may comprise reducing total cholesterol, low-density lipoprotein (LDL), and/or triglyceride levels, and may comprise increasing high-density lipoprotein (HDL) levels. The composition may reduce C-Reactive Protein (CRP) levels, which may be high-sensitivity CRP (hs-CRP) levels.

g. Dosage

A number of factors may lead to the plant flavonoid or additional agent being administered at a wide range of dosages. Depending on the potency of the plant flavonoid or additional agent in a desired application, the amount of plant flavonoid or additional agent present in the composition may be modified as necessary. The dosage of the plant flavonoid or additional agent may be from about 1 ng/kg to about 100 mg/kg, where "kg" indicates the body weight of the subject to which the composition is being administered. The dosage of the plant flavonoid or additional agent of the present invention may be at a dosage of about 1 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, or about 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, or 2000 mg/kg. In particular, the plant flavonoid may be eriocitrin, and optionally neoeriocitrin. The additional agent may be vitamin C, resveratrol, or the green tea extract.

The present invention has multiple aspects, illustrated by the following non-limiting examples.

EXAMPLE 1

Eriodictyol and Eriocitrin Complexes

An eriodictyol complex was extracted from citrus. The extracted eriodictyol complex had the following composition, as measured by high-performance liquid chromatography (HPLC).

| | |
|---|---|
| Eriocitrin | 0.41 |
| Hesperidin | 1.00 |
| Diosim | 0.31 |
| Eriodictyol | 91.32 |
| Hesperetin | 3.27 |
| Naringenin | 2.24 |
| Total bioflavonoids | 98.55 |

Figure 1:
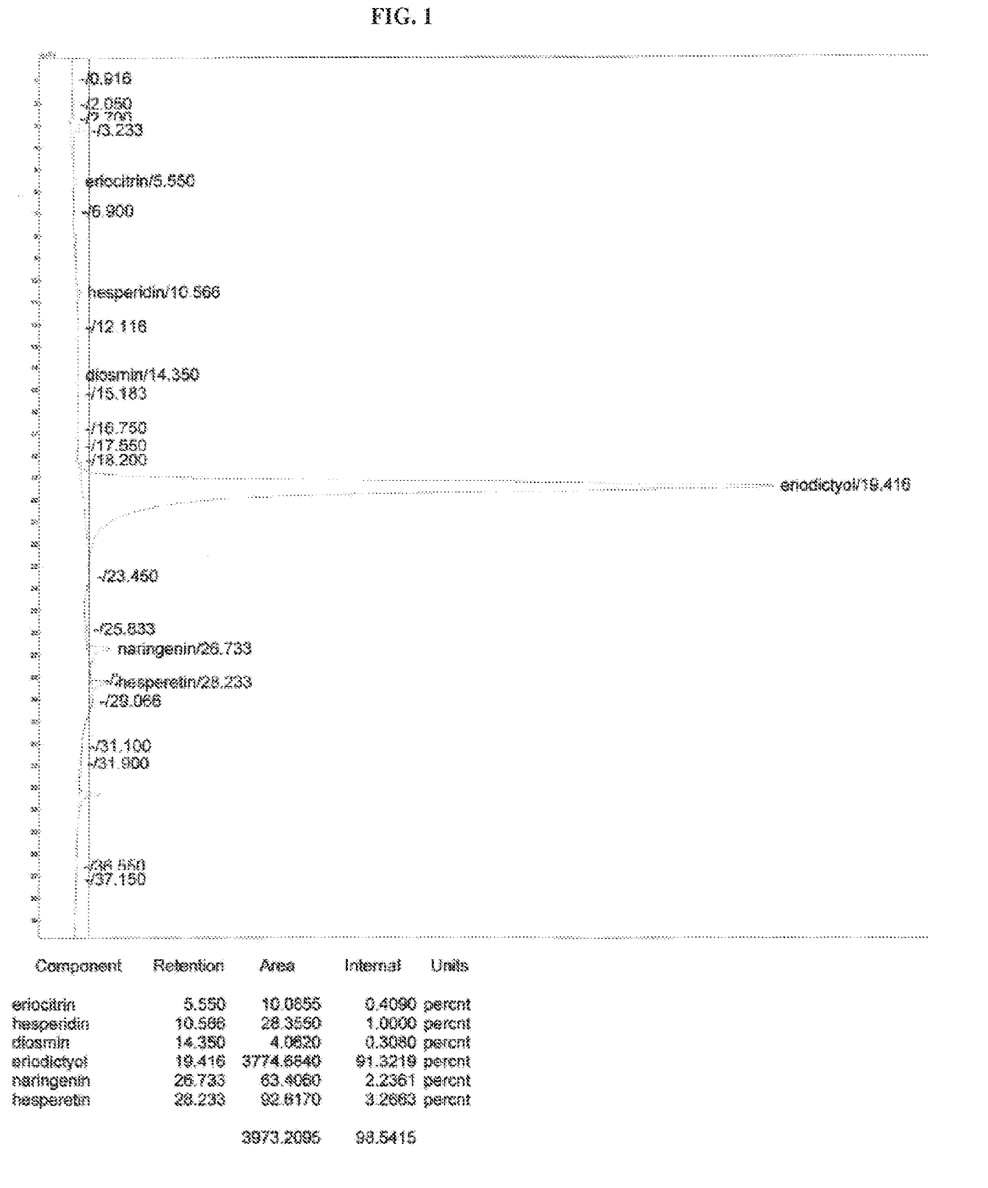
FIG. 1 shows the results of a high-performance liquid chromatography (HPLC) analysis of an eriodictyol complex.

The chromatograph of the analysis of the eriodictyol complex is shown in FIG. 1.

An eriocitrin complex was extracted from citrus. The extracted eriocitrin complex had the following composition, as measured by HPLC.

| | |
|---|---|
| Eriocitrin | 82.24 |
| Narirutin | 2.47 |
| Hesperidin | 6.52 |
| Didymin | 0.65 |
| Naringenin | 0.11 |
| Hesperetin | 0.03 |
| Other flavonoids | 2.69 |
| Total bioflavonoids | 94.71 |

EXAMPLE 2

Oxygen Radical Absorbance Capacity Assay

This example describes the anti-oxidant activity of the eriodictyol complex described in Table 1. Anti-oxidant activity was measured using an oxygen radical absorbance capacity assay for food and nutrition ($ORAC_{FN}$). The assay was performed using techniques known in the art, such as those disclosed in Ou, B. et al., J Agric and Food Chem, 2001, 49 (10): 4619-4626; Huang, D. et al., J Agric and Food Chem, 2002, 50 (7): 1815-1821; Ou, B. et al., J Agric and Food Chem, 2002, 50 (10): 2772-2777; Zhang, L. et al., Free Radic.Bio Med, 2007, 43 (suppl. 1): S17; Dubost, N.J. et al., Food Chem, 2007, 105 (2): 727-735; Zhang, L. et al., J Agric and Food Chem, 2009, 57(7): 2661-2667; and U.S. Pat. No. 7,132,296, the contents of all of which are incorporated herein by reference.

The activity of the eriodictyol complex against peroxyl radicals, hydroxyl radicals, peroxynitrite, super oxide anion, and singlet oxygen was measured. The total $ORAC_{FN}$ was also measured. The results are shown in Table 3.

| Test | Result | Units |
|---|---|---|
| Antioxidant power against peroxyl radicals | 19,643 | µmole TE/gram |
| Antioxidant power against hydroxyl radicals | 49,036 | µmole TE/gram |
| Antioxidant power against peroxynitrite | 1,322 | µmole TE/gram |

-continued

| Test | Result | Units |
|---|---|---|
| Antioxidant power against super oxide anion | 7,352 | µmole TE/gram |
| Antioxidant power against singlet oxygen | 6,888 | µmole TE/gram |
| Total $ORAC_{FN}$ (sum of above) | 84,241 | µmole TE/gram |

* The acceptable precision of the ORAC assay is <15% relative standard deviation
There are five predominant reactive species found in the body: peroxyl radicals, hydroxyl radicals, peroxynitrite, super oxide anion, and singlet oxygen. Total $ORAC_{FN}$ provides a measure of the total antioxidant power of a food/nutrition product against the five predominant reactive species.

Figure 2:
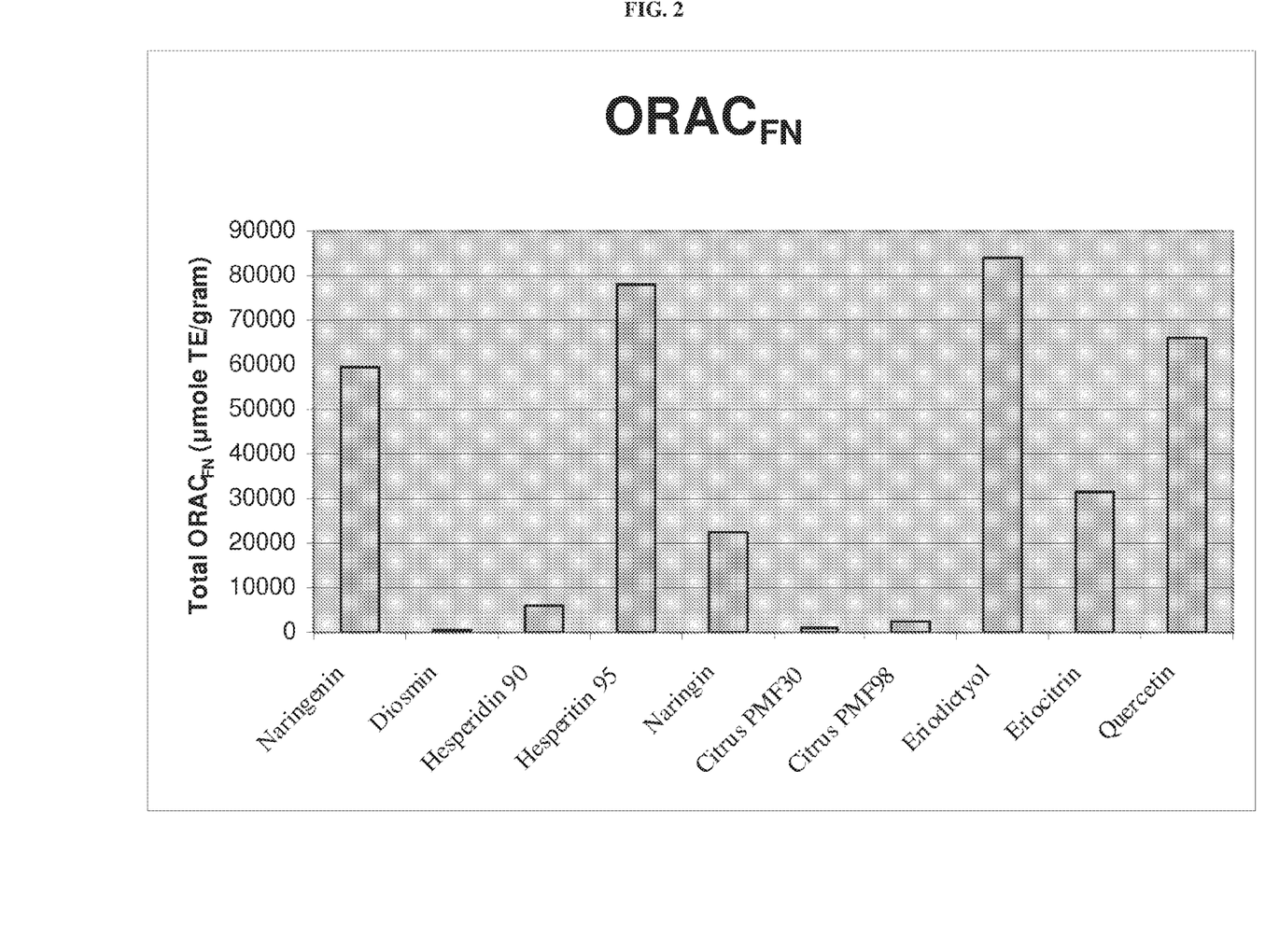
FIG. 2 shows the results of an oxygen radical absorbance capacity assay of the eriodictyol as compared to positive controls.

The activity of the eriodictyol complex was also compared against naringenin, diosmin, hesperidin 90, hesperetin 95, naringin, citrus polymethoxyolated flavone (PMF) 30, citrus PMF98, eriocitrin, and quercetin. The results of the comparison are shown in FIG. 2. The eriodictyol complex exhibited the highest total $ORAC_{FN}$ as compared to all other controls. The results indicate that the eriodictyol complex is a potent anti-oxidant.

EXAMPLE 3

Inhibition of NFkB

Figure 3:
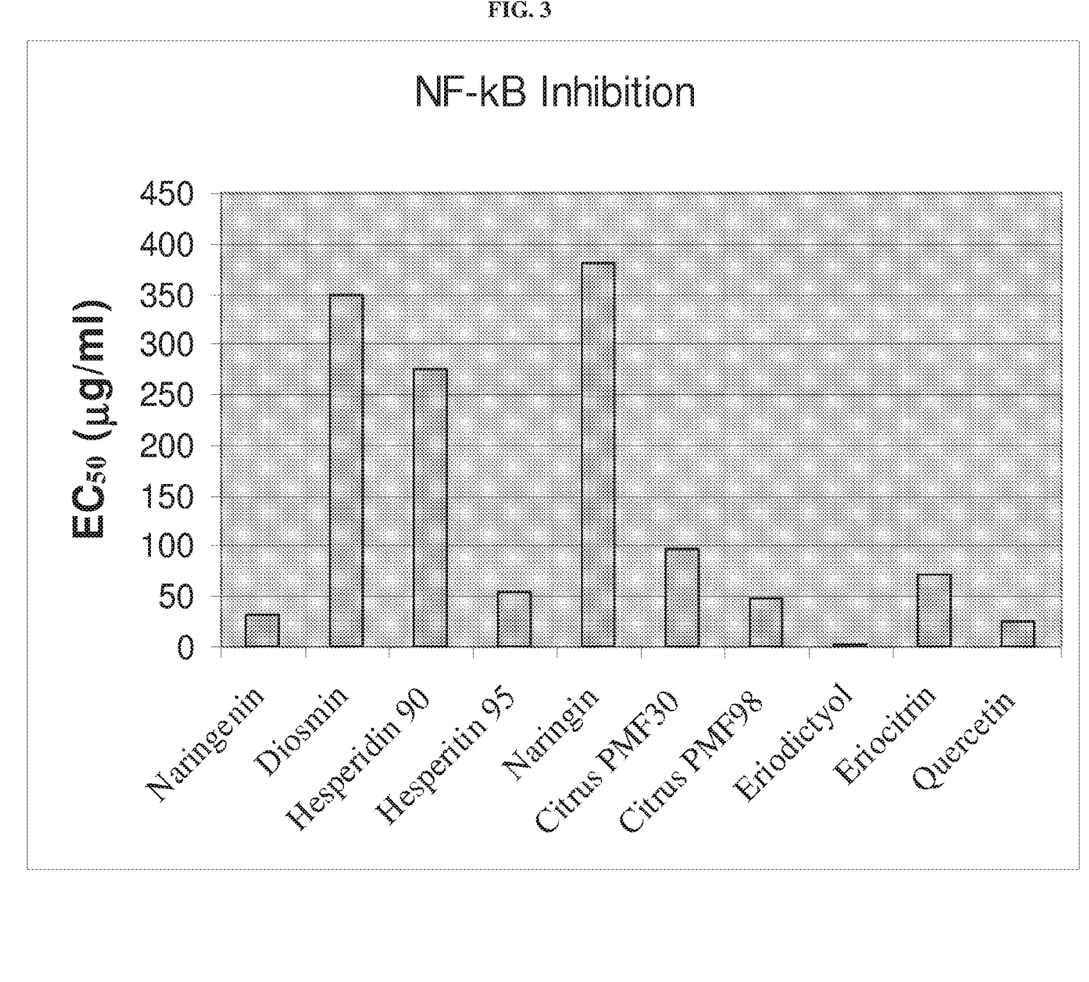
FIG. 3 shows the results of a NF-kB inhibition analysis of the eriodictyol complex as compared to positive controls.

This example demonstrates that the eriodictyol complex has NF-kB inhibitory activity. Activity of the complex was measured using a C2C12 cell line with a NF-kB-luciferase assay system (Affymetrix, Santa Clara, Calif.), and compared to a number of flavonoid controls. The results are shown in Table4 and in FIG. 3.

| Description | $EC_{50}$ (µg/ml) |
|---|---|
| Naringenin Lot#99080901 | 32.00 |
| Diosmin Lot#1095100101 | 348.83 |
| Hesperidin 90 Lot#890-19091102-1 | 275.70 |
| Hesperitin 95 Lot#20100101-HESTN | 54.23 |
| Naringin Lot#69591001 | 381.05 |
| Citrus Polymethoxylated Flavones 30 Lot#PMF-67606-30-NT | 96.73 |
| Citrus Polymethoxylated Flavones 98 Lot#39080602 | 48.53 |
| Eriodictyol Lot#ED-20100101 | 1.20 |
| Eriocitrin Lot#20100101-ER | 71.42 |
| Quercetin•2H2O Lot#80807 | 31.49 |

The eriodictyol had the highest level of NF-kB inhibitory activity as compared to all the controls. These results indicate that the eriodictyol complex has potent NF-kB inhibitory activity. A summary of the anti-oxidant and NF-kB inhibitory activity of the eriodictyol complex as compared to controls is shown in Table 5. The amounts shown are relative to quercetin.

| Description | BL ID | $E_{c5}0$ NF-kB | Compare quercetin | $ORAC_{FN}$ | Compare quercetin |
|---|---|---|---|---|---|
| Naringenin Lot#99080901 | 10-0725 | 32.00 | 0.78 | 59454 | 0.901 |
| Diosmin Lot#1095100101 | 10-0726 | 348.83 | 0.07 | 373 | 0.006 |
| Hesperidin 90 Lot#890-19091102-1 | 10-0727 | 275.70 | 0.09 | 6067 | 0.092 |
| Hesperitin 95 Lot#20100101-HESTN | 10-0728 | 54.23 | 0.46 | 77875 | 1.180 |
| Naringin Lot#69591001 | 10-0729 | 381.05 | 0.07 | 22389 | 0.339 |
| Citrus Polymethoxylated Flavones 30 Lot#PMF-67606-30-NT | 10-0730 | 96.73 | 0.26 | 1039 | 0.016 |
| Citrus Polymethoxylated Flavones 98 Lot#39080602 | 10-0731 | 48.53 | 0.52 | 2396 | 0.036 |
| Eriodictyol Lot#ED-20100101 | 10-0732 | 1.20 | 20.84 | 84241 | 1.276 |
| Eriocitrin Lot#20100101-ER | 10-0733 | 71.42 | 0.35 | 31355 | 0.475 |

This comparison indicates that the eriodictyol complex is 20-times more potent than quercetin in inhibiting NF-kB, and has over 1.2-fold higher anti-oxidant activity than quercetin.

EXAMPLE 4

Eriocitrin and Eriodictyol Reduce IL-6 and MCP-1 Levels

This Example shows that eriocitrin and eriodictyol compositions disclosed herein strongly reduce IL-6 and MCP-1 levels. The effects of eriocitrin and eriodictyol on anti-inflammatory markers were determined in mice fed a high-fat diet and compared to negative control, untreated mice that were fed either a standard- or high-fat-diet. Eriocitrin and eriodictyol effects were also compared against ibuprofen- and hesperidin-treated, high-fat-diet-fed mice. The effects of these various treatments on the cytokines IL-6, IL-10, MCP-1, and TNF-alpha are shown below.

| | Standard Diet | High Fat Diet | | | | |
|---|---|---|---|---|---|---|
| Cytokines | Without suplement | Without suplement | Ibuprofen | Hesperidin | Eriocitrin | Eriodictyol |
| IL-6 | $8.4 \pm 7.6^a$ | $66.9 \pm 53.9^b$ | $21.9 \pm 18.1^a$ | $5.9 \pm 4.6^a$ | $3.1 \pm 1.6^a$ | $5.7 \pm 2.7^a$ |
| IL-10 | $5.0 \pm 2.3$ | $4.2 \pm 1.1$ | $6.0 \pm 4.5$ | $5.3 \pm 2.4$ | $4.0 \pm 2.2$ | $4.7 \pm 1.6$ |
| MCP-1 | $22.8 \pm 7.3^a$ | $73.3 \pm 46.3^b$ | $43.4 \pm 31.5^{ab}$ | $27.6 \pm 9.0^a$ | $19.3 \pm 11.1^a$ | $14.1 \pm 6.3^a$ |
| TNF-alpha | $2.7 \pm 0.7$ | $2.9 \pm 0.8$ | $1.2 \pm 2.4$ | $2.7 \pm 0.3$ | $2.4 \pm 0.6$ | $2.0 \pm 0.2$ |

Mean ± standard deviation
Statistical differences between groups detected by ANOVA, where values followed by different letters differ significantly (p < .05).

Both eriocitrin and eriodictyol significantly reduced IL-6 and MCP-1 levels in high-fat-diet-fed mice in comparison to the negative controls. In fact, eriocitrin and eriodictyol reduced the levels of these cytokines more than either ibuprofen and hesperidin, and even reduced IL-6 and MCP-1 in high-fat-diet-fed mice to levels below those observed in standard-diet-fed mice. These data indicate that eriocitrin and eriodictyol are capable of strongly reducing levels of IL-6 and MCP-1.

EXAMPLE 5

Metabolic Syndrome

This example shows how the eriocitrin and ERIOMIN™ compositions described herein can improve symptoms of metabolic syndrome in humans. A clinical study is performed in which subjects undergo a one-week run-in period during which subject document baseline data. Subjects meeting the inclusion/exclusion criteria are enrolled in the study and sent a glucometer to determine their fasting blood glucose levels. Those meeting the study criteria are enrolled in the study.

The subjects fast for at least 10 hours, and their fasting glucose, fasting insulin, hs-CRP levels, and lipid panels (including LDL, HDL, and triglycerides) are measured. Following these baseline measurements, subjects consume (1) 50 mg-2 g/day eriocitrin; (2) 50 mg-2 g/day eriocitrin, 50-250 mg/day neoeriocitrin, 50-250 mg/day hesperidin; or (3) a placebo. After 30 days, the subjects' glucose, insulin, hs-CRP, and lipid panel measurements are taken after a ≥10 hour fast. In comparison to placebo-treated subjects, subjects who consumed eriocitrin/ERIOIMIN™ exhibit reduced glucose, insulin, and hs-CRP levels, as well as reduced total cholesterol and LDL levels and increased HDL levels.

EXAMPLE 6

Eriocitrin

An eriocitrin complex was extracted from citrus. The extracted complex had the following composition, as analyzed by HPLC on an "as-is" moist basis.

TABLE 7

| BIOFLAVONOIDS | % WT/WT |
|---|---|
| Eriocitrin* | 70.47 |
| Other Flavonoid | 3.02 |
| Narirutin | 3.58 |

TABLE 7-continued

| BIOFLAVONOIDS | % WT/WT |
|---|---|
| Hesperidin | 4.70 |
| Didymin | 0.91 |
| Total bioflavonoids | 82.68 |

Figure 4:
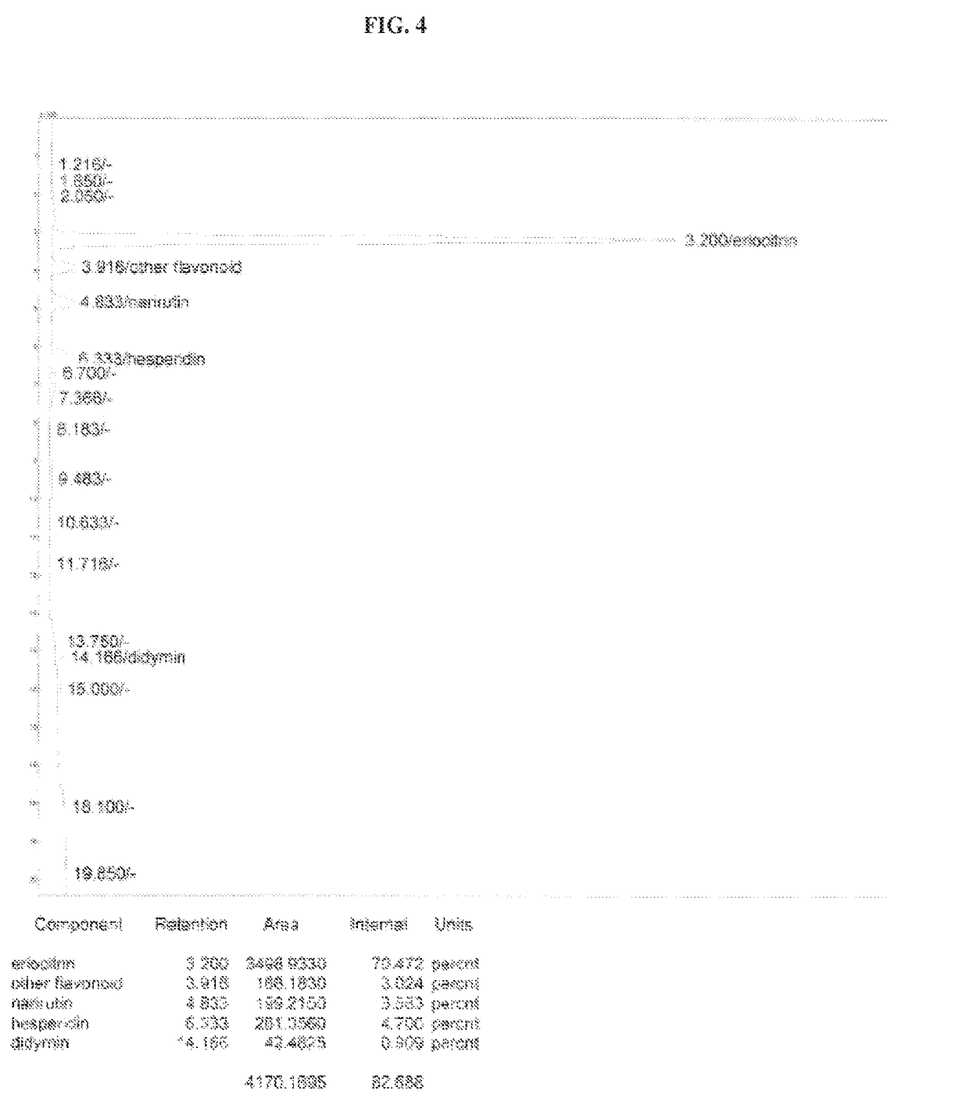
FIG. 4 shows the results of a HPLC analysis of an eriocitrin complex.

The eriocitrin was quantified using a response factor relative to hesperidin, and the eriocitrin content "as hesperidin" would be 62.92%. A chromatograph of the analysis of the eriocitrin complex is shown in FIG. 4.

The invention claimed is:

1. A method of reducing blood glucose levels in a human subject in need thereof, comprising administering to the subject a composition comprising 25-800 mg eriocitrin once per day.

2. The method of claim 1, wherein the composition comprises 25-200 mg eriocitrin.

3. The method of claim 2, wherein the composition comprises 50-100 mg eriocitrin.

4. The method of claim 3, wherein the composition comprises 40 mg eriocitrin.

5. The method of claim 3, wherein the composition comprises 70 mg eriocitrin.

6. The method of claim 1, wherein the blood glucose levels are fasting blood glucose levels.

7. The method of claim 1, wherein the subject has metabolic syndrome.

8. The method of claim 1, wherein the subject has diabetes.

9. A method of reducing blood glucose levels in a human subject in need thereof, comprising administering to the subject an oral formulation comprising 25-800 eriocitrin and an excipient once per day.

10. The method of claim 9, wherein the composition comprises 25-200 mg eriocitrin.

11. The method of claim 10, wherein the composition comprises 50-100 mg eriocitrin.

12. The method of claim 11, wherein the composition comprises 40 mg eriocitrin.

13. The method of claim 11, wherein the composition comprises 70 mg eriocitrin.

14. The method of claim 9, wherein the blood glucose levels are fasting blood glucose levels.

15. The method of claim 9, wherein the subject has metabolic syndrome.

16. The method of claim 9, wherein the subject has diabetes.

* * * * *